(12) United States Patent
Fumex et al.

(10) Patent No.: US 11,596,418 B2
(45) Date of Patent: Mar. 7, 2023

(54) ROTARY DRIVE TOOL FOR COUPLING OF A SURGICAL INSTRUMENT

(71) Applicants: Laurent Fumex, Madison, CT (US); Thierry Masseglia, La Garde (FR)

(72) Inventors: Laurent Fumex, Madison, CT (US); Thierry Masseglia, La Garde (FR)

(*) Notice: Subject to any disclaimer, the term of this patent is extended or adjusted under 35 U.S.C. 154(b) by 1029 days.

(21) Appl. No.: 16/351,696

(22) Filed: Mar. 13, 2019

(65) Prior Publication Data
US 2019/0307468 A1 Oct. 10, 2019

Related U.S. Application Data

(63) Continuation-in-part of application No. 15/439,242, filed on Feb. 22, 2017, now Pat. No. 10,743,847.

(51) Int. Cl.
*A61B 17/16* (2006.01)
*A61B 10/02* (2006.01)

(52) U.S. Cl.
CPC ........ *A61B 17/1628* (2013.01); *A61B 17/162* (2013.01); *A61B 17/1626* (2013.01); *A61B 10/025* (2013.01)

(58) Field of Classification Search
CPC . A61B 17/16; A61B 17/1613; A61B 17/1615; A61B 17/162; A61B 17/1622; A61B 17/1624; A61B 17/1628
See application file for complete search history.

(56) References Cited

U.S. PATENT DOCUMENTS

| 7,984,528 B2 | 7/2011 | Giacolo et al. |
| 8,944,069 B2* | 2/2015 | Miller ............... A61B 17/3472 |
| | | 128/853 |
| 2006/0142881 A1 | 6/2006 | Wang et al. |
| 2008/0045860 A1* | 2/2008 | Miller ................... A61B 46/10 |
| | | 600/567 |
| 2009/0194446 A1* | 8/2009 | Miller ................. A61B 10/025 |
| | | 606/86 R |
| 2019/0307468 A1* | 10/2019 | Fumex ................ A61B 17/162 |

FOREIGN PATENT DOCUMENTS

| FR | 3041239 | 3/2017 |
| WO | 2015154188 | 10/2015 |

OTHER PUBLICATIONS

Search Report dated Sep. 16, 2016.

* cited by examiner

*Primary Examiner* — Eric S Gibson
(74) *Attorney, Agent, or Firm* — Ipsilon USA, LLP

(57) ABSTRACT

A rotary drive tool for coupling of a surgical instrument, the rotary drive being intended to be enclosed within an envelope in such a way that the rotary drive tool can be used in a sterile environment. The rotary drive tool has a body with an end configured to removably engage the envelope intended to enclose the rotary drive tool. A coupling piece is disposed within the body, the coupling piece engaging and driving, in rotation, a surgical instrument.

15 Claims, 8 Drawing Sheets

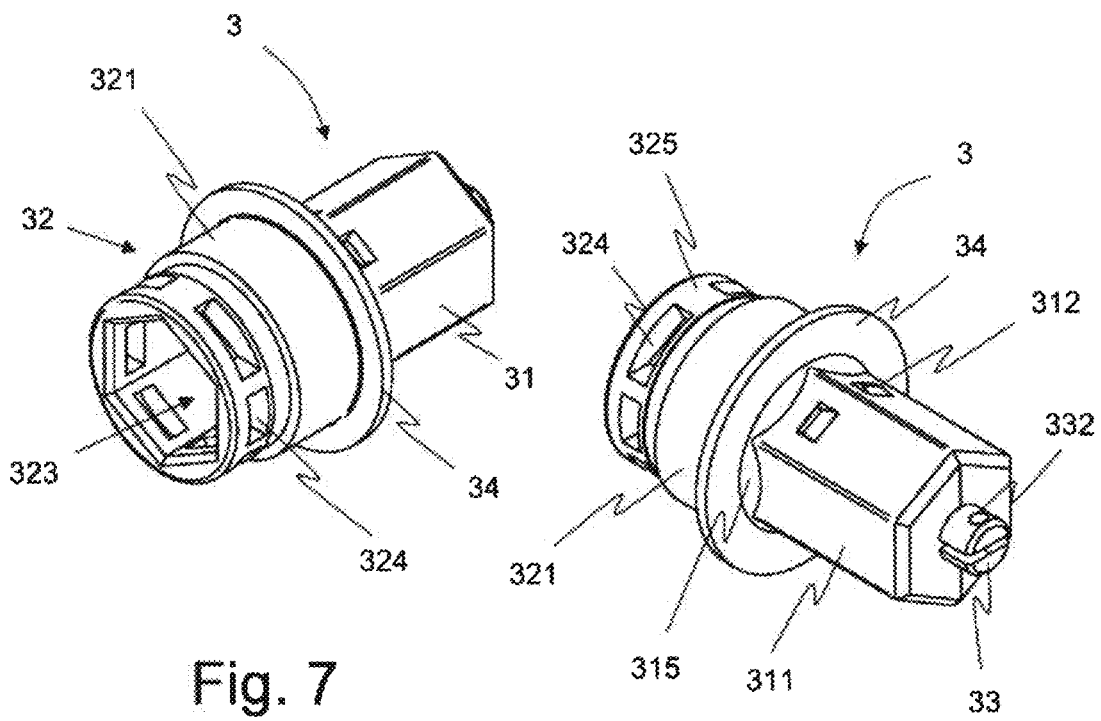
Fig. 7
Fig. 8
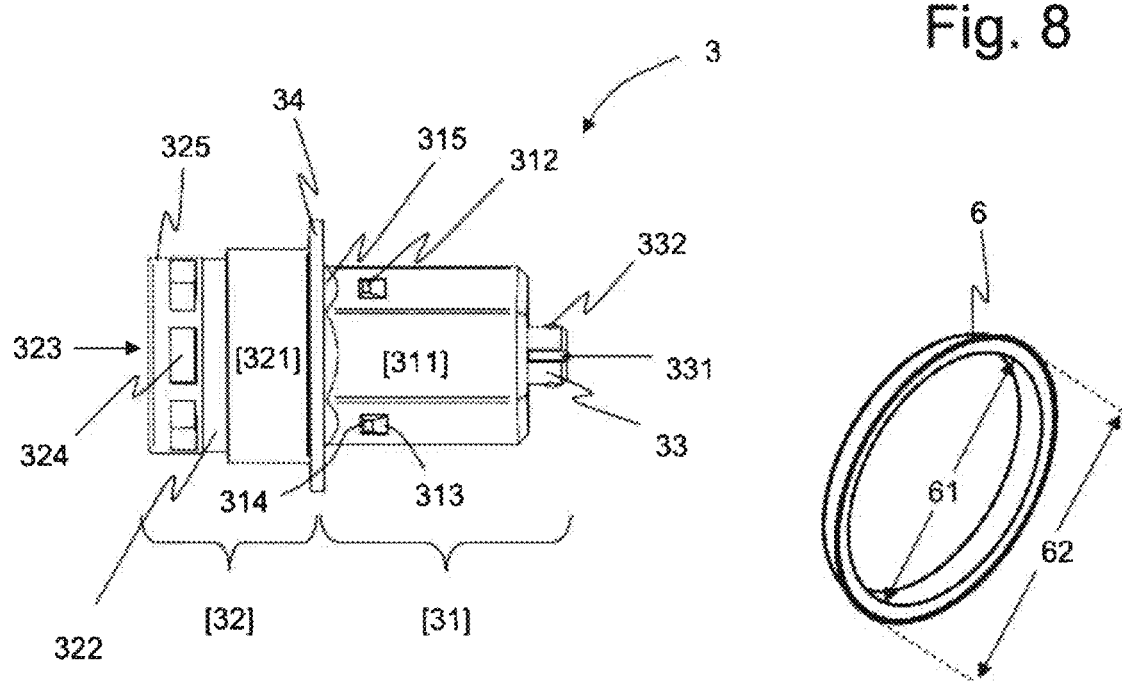
Fig. 9
Fig. 10

ROTARY DRIVE TOOL FOR COUPLING OF A SURGICAL INSTRUMENT

RELATED APPLICATION

This application is a continuation-in-part application of U.S. patent application Ser. No. 15/439,242, filed on Feb. 22, 2017, the entirety of which is incorporated by reference.

FIELD OF THE INVENTION

The invention relates to the general field of percutaneous surgical instruments. It relates more particularly to the percutaneous surgical instruments that are intended to pass through the epidermis and the soft tissue parts of the body in order, for example, to collect samples of bone marrow and of bone tissues for biopsy purposes.

Background of the Invention—Prior Art

In the field of percutaneous surgery and more particularly that of percutaneous bone biopsy, it is known to use various instruments with which it is possible to penetrate the soft tissue parts and then the cortical substance of the bone concerned and to collect samples of organic substances (bone marrow, bone specimens) contained in the bone or in the cavity of the latter.

These instruments are generally known as bone biopsy needles and bone marrow biopsy needles. They are generally composed of a cannula and a mandrel. The cannula may be used both as an access needle and a biopsy needle. In this case, the assembly formed by the cannula and the mandrel is placed through the soft tissue into the selected bone. Once in the bone, the mandrel is removed and the cannula is pushed forward according to the desire specimen length. Finally, the cannula is fully retrieved and the bone or bone marrow sample is ejected out of the cannula. In another case, a separate biopsy needle is used in addition to the cannula and its mandrel. In this latter example, the cannula and its mandrel (stylet) act as a percutaneous introducer to the bone. The introducer is placed through the soft tissue until bone is reached. An initial purchase in the cortex is performed. Once close to the lesion, the stylet is removed and a biopsy needle is placed inside the cannula. The biopsy is then performed with the biopsy needle through the cannula.

Through a percutaneous access, bone access needles are placed by the practitioner through the soft tissues and then into the selected bone.

These trocars generally have a hollow outer tube, of which the end is more or less sharp, and within which there slides a rod whose end is tapered in such a way as to perforate the bone, this rod possibly being configured to collect a sample of the tissue which is situated in the cavity.

Such instruments are generally used manually by way of a handle which is rigidly connected, permanently or non-permanently, to the proximal end (end not coming into contact with the bone) of the perforating rod, and which the practitioner turns into order to drill a hole in the bone. In practice, the practitioner brings the end of the outer tube of the trocar into contact with the bone and then rotates the handle in order to cause the end of the rod to penetrate the bone.

Thus, the international application published under the reference WO2006/061514 describes a trocar intended for bone biopsy and comprising an outer tube, of which the distal end is divided into two segments with a helical cutting edge, and in which a sharpened rod slides. This type of instrument is intended to be used manually via a handle.

The manual use of such a trocar, by means of a handle actuated directly by the practitioner, is a classical operating technique that allows the practitioner to finely control the perforation of the bone. However, in some circumstances, particularly when the hardness of the bone requires greater strength to cause the needle to penetrate the wall of the bone, it is sometimes more convenient, both for the patient and for the practitioner, to have available a drive tool, such as a drill, in order to cause the rod to penetrate the bone without application of excessive force.

It is therefore a considerable advantage for the practitioner to have available a trocar whose perforating rod can be actuated equally well by means of a simple handle or by way of a drive tool.

Such a possibility advantageously allows the practitioner to start a surgical procedure manually and then, if the hardness of the bone so requires, to complete the perforation by means of automatic rotational drive, without its being necessary to change the perforating rod and thus risk losing the point of entry into the bone.

However, it requires the availability of an interface device which is able, with one of its ends, to replace the handle used by the practitioner for manual use of the trocar; by fitting to the end of the latter identically to the handle, and by having at its other end an interface element on which the endpiece of a drive tool can be fixed removably.

The device envisioned here thus serves as a coupling element with which the trocar can be driven in rotation by means of a tool.

Among other functions, a device of this kind must be able to ensure relatively precise axial positioning of the drive tool with respect to the trocar, failing which the penetration precision of the trocar could be adversely affected.

In so far as the interface device is intended to ensure the connection of the end of a trocar (sterile and generally disposable item) to equipment of the drill type (naturally reusable and generally non-sterile item), such a possibility also requires that the interface device can be easily associated with means for mounting the drive tool on the end of the trocar and for driving said trocar in rotation while avoiding all contact between the trocar and the drive tool, which contact could cause contamination of one by the other.

The French patent application published under the reference FR 3007636 thus describes an interface system of a simple structure composed of a hexagonal male element, which is mounted on the proximal end of the trocar, and a hexagonal female element, in which the male element engages, the whole thing being joined together in a removable manner by a snap-fit action.

This document also describes how, depending on the rotary drive means in question, the hexagonal female element is either directly integrated in the handle (in the case of manual rotation of the trocar) or integrated in the end of an interface device mounted directly on the output shaft of the rotary drive tool (drill).

In both cases, the hexagonal female element advantageously retains similar morphological features (polygonal portion of the male and female elements) such that the end of the trocar can engage equally well in the handle or in the end of the tool.

Said patent application thus describes a simple and inexpensive interface system by which a trocar can be connected to a means for actuating the latter, which can equally well be a handle or a rotary drive tool. The connection established is a releasable connection permitting a precise axial alignment of the axis of rotation imposed by the actuator and of the axis of the trocar. However, the coupling device described in said application does not, as it stands, permit sterile coupling between the actuator and the trocar.

The U.S. Pat. No. 6,716,215 describes a means offering a solution for connecting a sterile drill bit to a non-sterile drill by way of a sterile bag. The sterile bag, on which a ring is fixed, is intended to receive a drill, allowing the latter to be packaged so that it can be used in a sterile environment.

In the area of connection of the drill to the drill bit, the leaktightness is provided by an O-ring seal, housed in the ring, which seals the body of the drill bit. Leaktightness is obtained by compression of the seal.

However, this solution has the disadvantage that the bag may find itself driven in rotation on account of the seal rubbing on the drill bit, and, by turning, it can the block the rotation of the drill.

The U.S. Pat. No. 7,850,620 describes a system by which a non-sterile drill accommodated in a sterile bag can be connected to a sterile biopsy instrument by means of a coupler which is rigidly connected to the bag. The coupler has a ring which is blocked in translation but free in rotation and on which the bag is welded. This solution does not permit complete leaktightness, since the ring may allow impurities to pass through on account of its functional play. Moreover, taking account of the structure of the coupler, such a device does not exclude the risk of the bag being driven in rotation by the rubbing action and of thus blocking the rotation of the drill.

The patent application published under the reference WO 2015/154188 also describes a system by which a non-sterile drill accommodated in a sterile bag can be connected to a sterile instrument by means of a ring which is integrally connected to the bag and by means of a coupling shaft mounted in the ring. The ring is formed by two concentric hoops screwed onto each other in such a way as to enclose the bag in the area of an opening in the latter, permitting the passage of the coupling shaft through the bag. The leaktightness between the outside and the inside of the bag is provided by an attached seal which is accommodated in the area of the coupling shaft so as to come into contact with the ring when the coupling shaft interacts with the ring.

A major disadvantage of this system lies in the fact that the ring is not designed to be rigidly connected to the drill, with the result that the bag can be driven in rotation by the rubbing action and can thus block the rotation of the drill.

Moreover, the design of the ring and of the coupling shaft is complex, which results in expensive manufacture and assembly of the system parts. Indeed, the ring and the coupling shaft comprise multiple parts which need to be assembled before the instrument is mounted on the drill, in particular by screwing the hoops together and by mounting the ball bearing on the coupling shaft. Moreover, the placement of the seal requires machining to be performed on the coupling shaft and on the ring, which adds to the manufacturing costs.

OBJECT AND SUMMARY OF THE INVENTION

An object of the invention is to propose a solution for connecting a sterile drill bit to a non-sterile drill through a sterile bag, overcoming at least partially the aforementioned disadvantages.

To this end, the invention relates to a device for sterile coupling of a percutaneous surgical instrument to a rotary drive tool for said instrument having an end provided with a coupling piece. This device has:

a flexible envelope with a first opening of circular shape and with a second opening allowing the drive tool to be introduced into said envelope, the first opening being positioned on the wall of the envelope in such a way that, when the drive tool is located in the pouch, the coupling piece is located opposite said first opening;

a connector piece having a cylindrical distal portion, for coupling to the percutaneous surgical instrument, and a proximal portion, for coupling to the drive tool, the connector piece being configured to pass through the envelope via the first, circular opening in such a way that the end of its distal portion is placed outside the envelope, its proximal portion being placed inside the envelope;

a tubular ring which forms a conduit, in which the connector piece is intended to be inserted, the ring being positioned on the inner surface of the envelope opposite the first, circular opening, said ring being rigidly connected to the envelope via one of its ends, its other end being configured to rigidly connect the envelope to the wall of the drive tool, said conduit being configured in such a way that the connector piece can turn freely about its axis inside the ring while being held in place axially.

According to the invention, the envelope, the ring and the connector piece have means which interact in order to form a leaktight barrier in the area of the first, circular opening, said barrier being configured so as not to impede the rotation of the connector piece.

According to various configurations that may be considered separately or in groups, the device according to the invention can have the following features.

According to one particular feature, the distal portion of the connector piece has a tubular shape and has an indentation configured to receive the proximal end of a percutaneous surgical instrument, the end of the proximal portion of the connector piece being configured so as to be able to fit in the coupling piece of the drive tool.

According to another feature, the ring has a disc-shaped flange situated at the end of the tubular part via which said ring is fixed on the inner wall of the envelope, the flange having a central opening whose centre is situated on the axis of symmetry of the tubular part, the ring and the flange being fixed to the inner wall of the envelope in such a way that the centre of the first opening is also aligned with the axis of symmetry of the tubular part.

According to another feature, with the ring having the above features, the connector piece additionally has an annular protuberance positioned on its outer surface and delimiting the distal portion and the proximal portion, the external diameter of the annular protuberance being substantially equal, except for functional play, to the internal diameter of the tubular body of the ring and greater than the diameter of the opening of the flange, in such a way that the connector piece can slide in the ring along an axis substantially coincident with the axis of symmetry of the tubular body and pass through the flange until the annular protuberance comes into abutment on the inner wall of the flange, the axis of symmetry of the connector piece then being maintained substantially coincident with the axis of symmetry of the tubular body by the annular protuberance, the flange, the inner wall of the tubular body of the ring and the annular protuberance of the connector piece forming a baffle, limiting the possibility of fluids or solids passing between the inside and the outside of the envelope through the first opening.

According to another feature, the first opening of the flexible envelope has a diameter slightly smaller than the external diameter of the cylindrical distal portion of the connector piece, said diameter being defined in such a way that, when the connector piece is inserted into this opening from the inside of the envelope, the edge of said first opening deforms and constitutes an annular fold which is directed to the outside of the envelope and which will surround the outer surface of the cylindrical body of the distal portion of the connector piece, this fold constituting a seal which interacts with the baffle formed by the flange of the ring, the inner wall of the tubular body of the ring and the annular protuberance of the connector piece in order to constitute a leaktight barrier in the area of the first opening of the envelope.

According to another feature, with the body of the drive tool having a conical shape at the end provided with the coupling piece, the end of the tubular ring has an opening of conical shape dimensioned in such a way that, when the end of the drive tool is inserted into the ring, this insertion brings about a tight engagement of the ring on the end of the drive tool, which blocks any translation and/or rotation movement of the envelope with respect to the drive tool.

According to another feature, with the wall of the end of the body of the tool having a longitudinal protuberance forming a wedge, the inner wall of the tubular ring has a longitudinal notch dimensioned to receive said wedge, the wedge/notch assembly forming a complementary means of blocking the rotation movement of the envelope with respect to the drive tool.

According to another feature, with the coupling piece of the drive tool forming a cavity with a rear zone of hexagonal shape and a front end of frustoconical shape, the proximal portion of the connector piece forms a male element of hexagonal cross section, dimensioned in such a way as to be able to be inserted, with minimum play, into the cavity of hexagonal cross section of the coupling piece, the outer wall of the proximal portion of the connector piece having a frustoconical zone formed on said outer wall and designed to interact with the frustoconical front end of the coupling piece, so as to ensure that the coaxiality of the two elements is maintained during use.

According to another feature, with the inner wall of the cavity of the coupling piece of the drive tool having a chamfered groove in the area of the hexagonal rear zone, the body of the proximal portion of the connector piece has chamfered bosses designed to be able to fit in said chamfered groove and ensure that the body of the proximal portion of the connector piece is blocked with a snap-fit action in the coupling piece.

According to another feature, with the cavity formed by the coupling piece of the drive tool having a blind cylindrical bore which forms the bottom of the cavity and of which the axis of symmetry is coincident with the general axis of symmetry of the coupling piece, the body of the proximal portion of the connector piece has, at its end, a cylindrical end element which is slit along its length, and of which the diameter is defined in such a way that its insertion into the blind cylindrical bore is effected with minimum play.

According to another feature, the outer wall of the end element of the body of the proximal portion of the connector piece has bosses forming overthicknesses, such that the diameter of the cross section of the end element is locally greater than the diameter of the bore of the coupling piece of the drive tool and such that the engagement of the end element of the body of the proximal portion of the connector piece is effected without play.

According to another feature, the distal end of the connector piece has a hexagonal indentation for receiving the proximal end of a percutaneous surgical instrument, this proximal end having a connector piece of hexagonal cross section.

According to another feature, the cylindrical body of the distal portion of the connector piece has an annular groove for receiving an indicator ring, said indicator ring being arranged on the cylindrical body in such a way that, when the coupling is obtained, if the leaktight barrier in the area of the first opening of the envelope is effective, the indicator ring is visible to the practitioner.

According to another feature, the tubular ring is formed in one piece.

According to another feature, the tubular ring is positioned on the inner surface of the envelope and rigidly connected to the envelope via one of its ends, such that the the whole of the tubular ring is disposed inside the envelope when the drive tool is located in the envelope.

The invention also relates to a method for carrying out the sterile coupling of a biopsy instrument and of a drive tool for said instrument by means of a coupling device according to the invention, the method comprising the following steps:
  a preliminary step in which the envelope is turned back on itself, this step being carried out by pushing the ring inside the envelope until its free end emerges from the envelope through the second opening of the envelope;
  a first step during which the assistant places the coupling piece of the drive tool on the proximal end of the connector piece until the two elements engage one inside the other;
  a second step during which the practitioner takes hold of and presents the turned-back envelope and during which the assistant, having introduced the distal end of the drive tool into the ring of the envelope, lets go of the drive tool, the latter then being held by the practitioner via the turned-back envelope such that, on account of the weight of the drive tool, the envelope partially recovers its unfolded form;
  a third step during which the practitioner finishes reshaping the envelope without touching the drive tool, such that it encloses the drive tool, then hermetically closes the second opening of the envelope;
  a fourth step during which the practitioner fits the percutaneous surgical instrument in place by inserting the connector piece of said instrument into the end of the connector piece.

According to a particular arrangement, with the coupling device being delivered to the practitioner in a sterile package, with its envelope already turned back, the preliminary step is implemented independently at the time of packaging of the coupling device.

The invention also relates to a rotary drive tool for coupling of a surgical instrument, the rotary drive being intended to be enclosed within an envelope in such a way that the rotary drive tool can be used in a sterile environment, the rotary drive tool comprising:
  a body comprising an end configured to removably engage the envelope intended to enclose the rotary drive tool,
  a coupling piece disposed within the body, the coupling piece being configured to engage and drive in rotation a surgical instrument.

According to another feature, the end of the body is configured to removably engage a ring fixed to a bag comprising an opening to receive the surgical instrument the ring and the bag forming the envelope.

According to another feature, the end of the body is configured to prohibit any movement of rotation of the ring relative to the end of the body.

According to another feature, an outer surface of the end of the body comprises a longitudinal wedge configured to engage a longitudinal notch of the ring to prohibit any movement of rotation of the ring relative to the end of the body According to another feature, the end of the body has a conical shape.

Another object of the invention is to propose a solution for securely connecting a non-sterile drill to a sterile envelope in a cleaner manner.

To this end, the invention also relates to a rotary drive tool for coupling of a surgical instrument, the rotary drive being intended to be enclosed within an envelope in such a way that the rotary drive tool can be used in a sterile environment, the rotary drive tool comprising:
  a body comprising an end configured to removably engage the envelope intended to enclose the rotary drive tool,
  a coupling piece disposed within the body, the coupling piece being configured to engage and drive in rotation a surgical instrument,
  wherein the end of the body entirely covers the coupling piece such that the coupling piece does not extend from the end of the body.

According to another feature, the rotary drive tool further comprises:
  a motor to drive in rotation the coupling piece,
  a reducer disposed between the motor and the coupling piece to set the rotation speed and the torque transmitted to the coupling piece by the motor.

According to another feature, the body comprises an upper portion having a central part enclosing the motor and the reducer, the central part having a circular cross-section.

According to another feature, the rotary drive tool further comprises:
  an accumulator to supply electricity to the motor,
  a control circuit configured to control the motor, the reducer and the accumulator.

According to another feature, the body comprises a lower portion forming a handle of the rotary drive tool 5 and enclosing the accumulator and the control circuit.

According to another feature, the reducer has a speed reducing ratio between 85:1 and 110:1, most preferably of 100:1.

According to another feature, the motor and the reducer are configured to make the coupling piece to rotate at a rotation speed between 170 et 230 RPM, most preferably of 200 RPM.

According to another feature, the motor and the reducer are configured to transmit to the coupling piece a torque between 3.5 and 7 Nm, most preferably of 4 Nm.

BRIEF DESCRIPTION OF THE FIGURES

The features and advantages of the invention will be better understood from the following description with reference to the attached figures, in which:

FIGS. 7 to 9 show schematic perspective views of the connector piece of the coupling device according to the invention in the embodiment in question;

FIG. 10 shows a schematic perspective view of an indicator ring intended to form part of the device according to the invention in the embodiment in question.

It should be noted that, in the figures, an element with the same function or structure is always identified by the same reference to the text.

DETAILED DESCRIPTION

To explain the various aspects of the invention with clarity, the following description sets forth the various features of the coupling device according to the invention on the basis of a particular embodiment which is taken as an example and its use for carrying out the sterile coupling of a biopsy instrument to a drive tool.

However, it will be appreciated that the scope of the invention is limited only by the combination of the features in the claims and is not in any way limited to these illustrative embodiments and examples of use.

Figure 1:
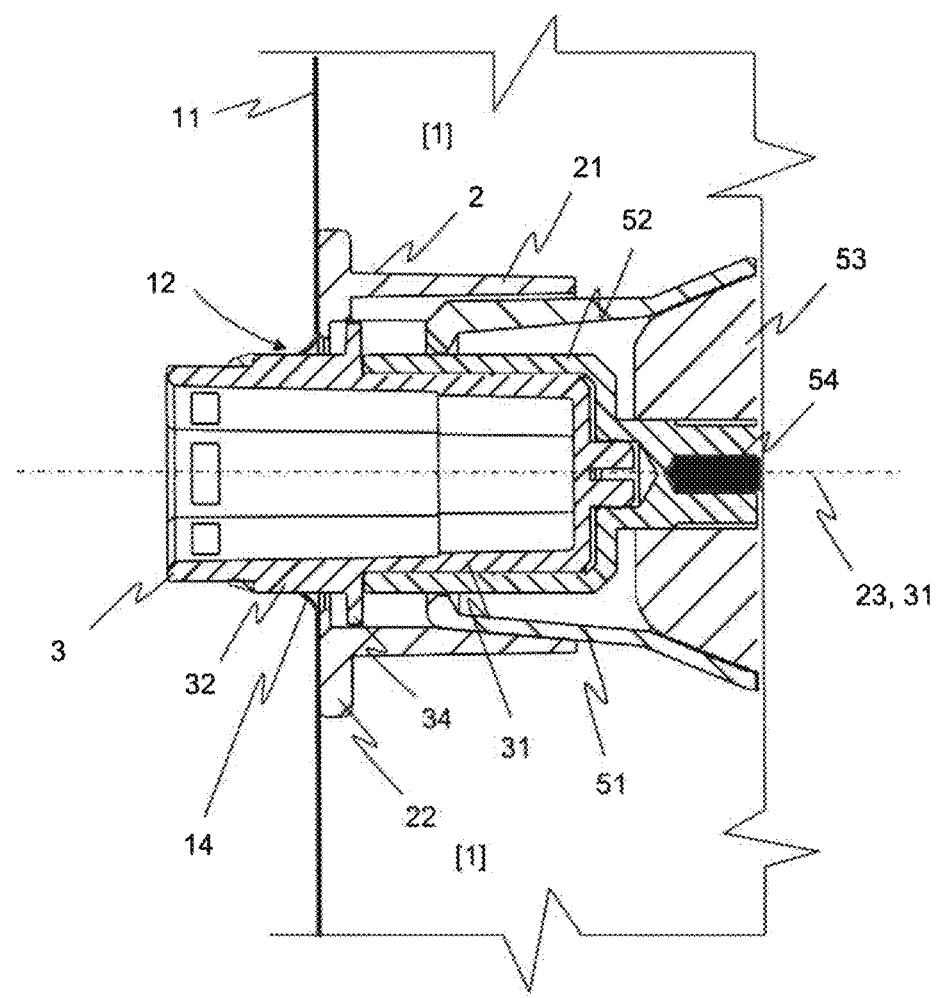
FIG. 1 shows a partial sectional view of the coupling device according to the invention, in the area of the zone of insertion of the end of a surgical instrument into the connector piece of the device.

Reference will first be made to FIG. 1, which sets forth the general technical features, functions and dimensions of the coupling device according to the invention. As is illustrated in FIG. 1, the coupling device principally comprises:
  an envelope 1 intended to enclose the rotary drive tool in such a way that the latter can be used in a sterile environment without its introduction into this environment being able to contaminate the latter,
  a connector piece 3 ensuring the actual connection between the end of a rotary drive tool 5, accommodated inside the envelope 1, and the surgical instrument which the drive tool is intended to drive and which is placed outside the envelope. For this purpose, the connector piece 3 is configured and arranged within the device in such a way as to pass through the wall of the envelope 1.

Figure 4:
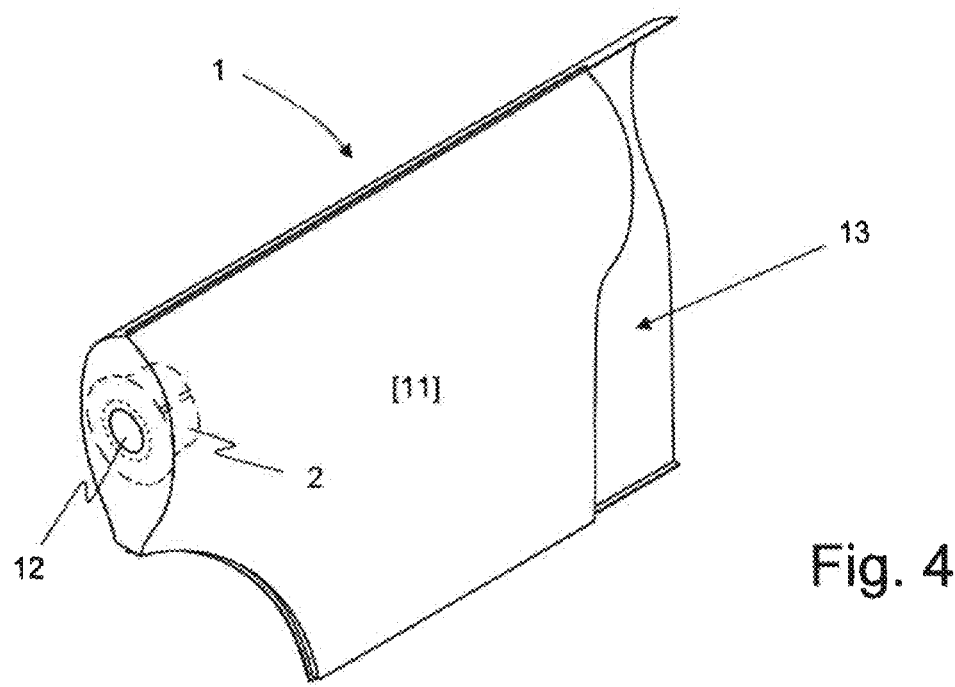
FIG. 4 shows a schematic perspective view of the envelope of the coupling device according to the invention in a particular embodiment, adapted in particular to the drive tool of FIGS. 2 and 3.

The envelope 1 of the coupling device according to the invention, illustrated in more detail by the schematic perspective view in FIG. 4, has a bag 11 in the form of a pouch which is intended to serve to accommodate the drive tool and has, on one of its walls, a circular orifice 12 (which is shown with the element 3 passing through it in FIG. 1).

The bag 11 also has a second opening 13 (not shown in FIG. 1), which is dimensioned to allow a drive tool to be easily inserted inside the bag, this opening being provided with a closure means for reclosing said opening in a leaktight manner.

The envelope 1 also has a ring 2, which itself has a tubular part 21 forming a conduit 211. The ring 2 is configured so as to be able to be fixed removably on the end 51 of the body 53 of the drive tool 5, in such a way that the assembly the ring 2 and the body 53 of the drive tool 5 are rigidly connected to each other. The ring 2 can be fixed on the body of the drive tool by any suitable means that can be placed, for example, inside the ring.

According to the invention, the ring 2 is fixed to the inner wall of the bag 11 via one of its ends, in the area of the opening 12, in such a way that the centre of the opening 12 is aligned with the axis of symmetry 23 of the tubular part 21 of the ring. In particular, the tubular ring 2 is positioned on the inner surface of the envelope 1 and is rigidly connected to the latter via one of its ends 22, such that the whole of the tubular ring 2 is disposed inside the envelope 1 when the drive tool is located in the envelope 1. In other words, no portion or part of the tubular ring 2 is disposed outside the envelope 1 when the drive tool is located in the envelope 1. This inner position of the tubular ring 2 makes it possible in particular for a minimal space to be taken up outside the envelope 1, in particular in relation to a tubular ring that has an outer portion, as in the document WO 2015/154188 described above.

Moreover, the tubular ring 2 can be formed in one piece. Thus, the joining of the tubular ring 2 to the envelope 1 is made easy compared to a ring that has several pieces to be assembled. In this first case, only one piece has to be handled in order to rigidly connect the tubular ring 2 to the envelope 1.

The connector piece 3 is an element of elongate shape having a symmetry of revolution about its longitudinal axis 31 (coincident with the axis 23 in FIG. 1). During the assembly of the various elements of the coupling device according to the invention, it is positioned so as to pass through the wall of the bag 11 via the opening 12, by passing through the inside of the ring 2.

The connector piece 3 has a cylindrical distal portion 32, of which a part 321 of circular cross section is intended to be placed at least partially outside the envelope 11 when the connector piece 3 is put in place, and a proximal portion 31 intended to take up a position inside the envelope 1.

Thus, according to the invention, the end of the distal portion 32 is configured so as to constitute a mechanical interface between the connector piece 3 and the end of a surgical instrument, while the end of the proximal portion 31 is configured so as to constitute a mechanical interface between the connector piece 3 and the coupling piece 52 of the drive tool 5. Depending on the adopted interface configuration, the end of the proximal portion 31 is configured to be fixed on or in the coupling piece 52 of the rotary drive tool 5 in question.

Also according to the invention, these interfaces are equipped with blocking means which, during the operation and in the absence of any action by the practitioner, make it possible to maintain the mechanical bonds between the connector piece and the surgical instrument, on the one hand, and between the connector piece and the drive tool, on the other hand.

Also according to the invention, they are likewise provided with means by which the axes of symmetry of the percutaneous surgical instrument, of the connector piece of the device according to the invention and of the coupling piece of the rotary drive tool are kept collinear.

The connector piece 3 is configured and dimensioned, taking account of the internal dimensions of the ring 2, so as to be able to turn freely inside the ring 2.

It additionally has a translation-blocking means 34 which is configured to interact with the ring 2 so as to limit its movement of translation inside the ring, such that it cannot come completely out of the bag 11 through the opening 12.

In a preferred embodiment of the invention, the blocking means 34 is likewise configured and arranged to keep the connector piece in a position for which its axis of symmetry 31 is substantially coincident with the axis of symmetry 23 of the tubular part 21 of the ring 2, when the connector piece 3 is in place in the ring 2.

The diameter of the distal portion 32 is, for its part, defined so as to be slightly greater than the diameter of the opening 12 formed in the wall of the envelope 1, such that the insertion of the end of the distal portion of the connector piece into the opening 12 leads to an elastic deformation of the latter, forming a fold 14 around the outer wall of the part 321 of circular cross section of the distal portion 32. This fold advantageously constitutes a seal arranged in the area of the first opening 12 of the envelope. Thus, the leaktightness between the outside and the inside of the envelope 1 is provided by the envelope 1 itself. This allows the coupling device to function without the addition of an attached seal and without manufacturing steps permitting the assembly thereof. Such leaktightness provided directly by the envelope 1 reduces the difficulty involved in manufacture and assembly, particularly in relation to a system in which the leaktightness is provided by an attached seal that is mounted inside machined grooves.

FIGS. 2 to 10 show in greater detail not only the main technical features of the invention, but also additional technical features, and they do so particularly, though not exclusively, in relation to one embodiment taken as an example.

Figure 2:
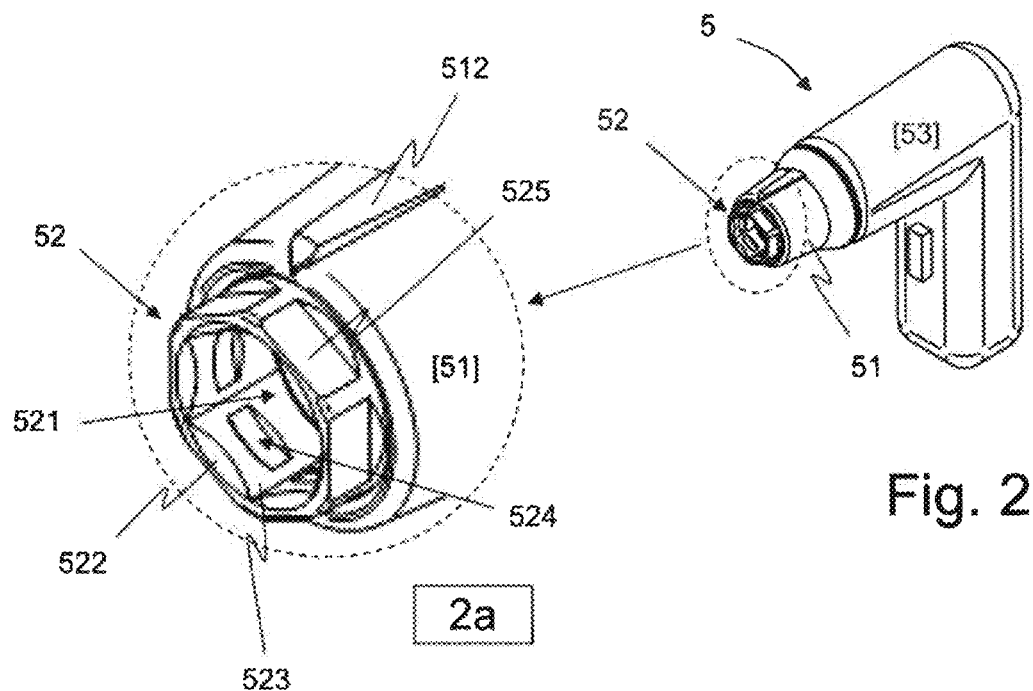
FIGS. 2 and 3 show schematic perspective views illustrating an example of a drive tool equipped with a connector piece allowing it to be coupled to a biopsy instrument.
Figure 3:
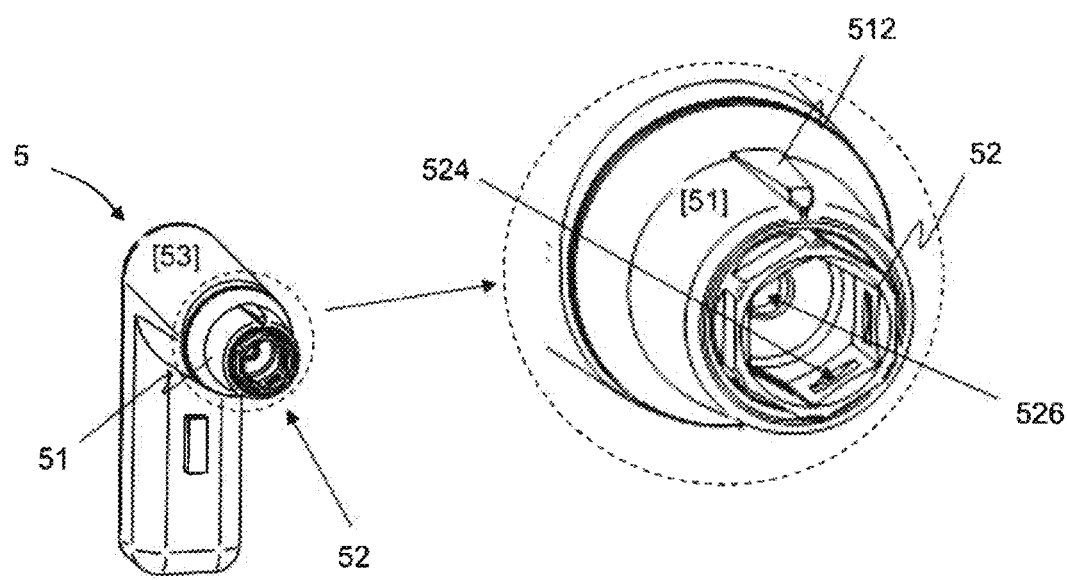

This embodiment is adapted in particular to the sterile coupling of a biopsy instrument to a particular rotary drive tool having a coupling piece such as the one illustrated in FIGS. 2 and 3.

The example of the drive tool 5, illustrated in FIGS. 2-2a and 3-3a, has a body 53 (shown schematically) with a conical end 51 from which emerges a coupling piece 52 which is mounted freely in rotation with respect to the body 53 of the tool 5.

In a preferred embodiment corresponding to the illustrative embodiment shown, the end 51 of the body 53 of the drive tool has, on its wall, a longitudinal wedge 512.

Generally, the coupling piece 52, for its part, is configured in such a way as to be able to be joined mechanically to the connector piece 3 of the coupling device according to the invention.

This coupling piece 52, driven in rotation by the drive shaft 54 (see FIG. 1) of the drive tool 5 on which it is mounted when the drive tool is set in motion, is configured in such a way that it constitutes a mechanical interface with the end of the surgical instrument that it is intended to drive in rotation.

In the illustrative embodiment considered here, the coupling piece 52 is in the form of a cavity 521 with an inner wall which has a rear zone 523 of hexagonal shape and a front end 522 of frustoconical shape.

Moreover, a chamfered groove 524 is formed in the inner wall of the cavity 521 in the area of the hexagonal rear zone 523.

The coupling piece 52 likewise has a blind cylindrical bore 526 which forms the bottom of the connector piece, and of which the axis of symmetry is coincident with the general axis of symmetry of the coupling piece 52.

It additionally has an outer wall 525 of hexagonal cross section, of which the faces are disposed opposite the faces forming the hexagonal rear zone 523 of the inner wall of the coupling piece 52. Such an arrangement serves advantageously as a visual indicator for correctly orienting the coupling piece 52 in order to facilitate the insertion of the drive means 5 on the end of the connector piece 3.

FIG. 4 shows a schematic perspective view of the envelope 1 equipped with its ring 2 according to the invention.

As has been described above, the envelope 1 has a bag 11 which is in the form of a pouch intended to receive the drive tool 5, and on the wall of which the ring 2 (shown in dotted lines) is fixed opposite the opening 12.

It will be noted that the opening 12 is preferably positioned on the wall of the bag 11, as illustrated in FIG. 4, in such a way as to facilitate the insertion of the end 51 of the drive tool 5 in the tubular part 21 of the ring 2 when said tool is introduced into the bag 11.

Figures 5, 6:
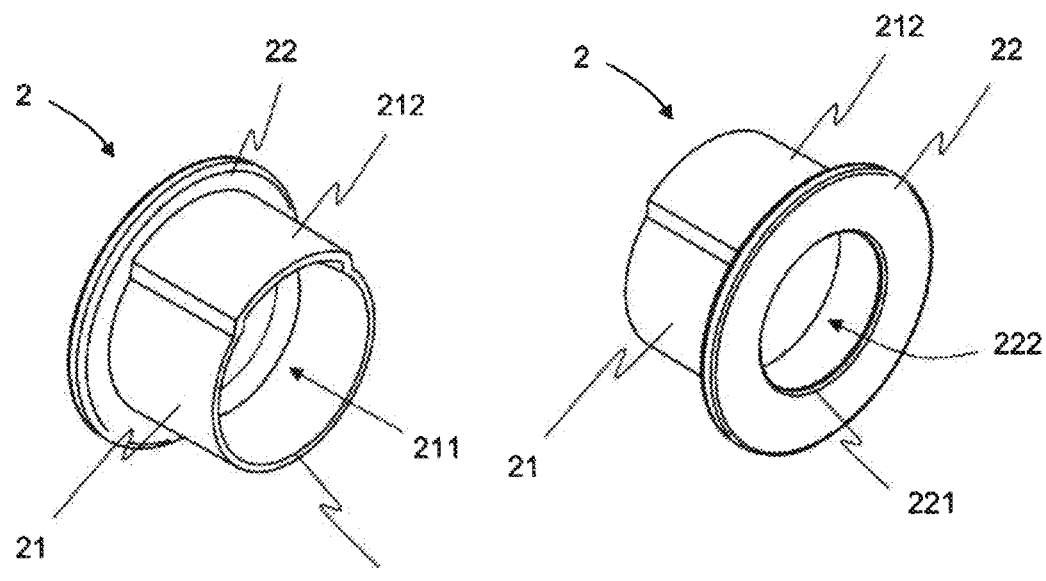
FIGS. 5 and 6 show schematic perspective views illustrating the ring of the envelope of the coupling device according to the invention in the embodiment corresponding to FIG. 4.

As is illustrated in FIGS. 5 and 6, the ring 2 in this illustrative embodiment has a tubular body 21 and an end flange 22, the tubular body 21 forming an internal conduit 211 in which the end 51 of the body of the rotary drive tool 5 engages in such a way that the ring 2 and the end 51 of the body of the tool 5 are mechanically joined to each other.

The disc-shaped flange 22 is placed at the end of the tubular body 21 of the ring 2 in contact with the wall of the envelope 1. It has a central opening 222, which is preferably circular, and of which the centre is situated on the axis of symmetry 23 of the tubular body 21.

Thereafter, the ring 2 is fixed on the inner wall of the bag 11 via its end flange 22, in the area of the opening 12, in such a way that the centre of the opening 12 is aligned with the axis of symmetry of the tubular body 21 of the ring.

Preferably, the cross section of the opening 222 is smaller than the cross section of the internal conduit 211, such that the wall of the flange forms an inner collar which constitutes a circular abutment at the end of the tubular body 21.

In the present illustrative embodiment, the conduit 211 has a conical shape interacting with the conical shape of the end 51 of the body 53 of the rotary drive tool 5, as shown in FIGS. 2-2*a* and 3-3*a*.

The conicities of the two conical shapes are here defined in such a way that, when the end 51 of the body of the drive tool 5 is inserted into the conduit 211, the two elements 21 and 51 wedge one inside the other, which tends to keep the ring 2, clamped on the end 51 of the body of the drive tool 5, in a fixed position with respect to the latter.

In the embodiment described here, the tubular body 21 is additionally configured to permit the introduction, into the conduit 211, of the longitudinal wedge 512 placed on the outer surface of the end 51 of the body of the drive tool 5. For this purpose, the wall of the conduit 211 has a longitudinal notch 212 intended to receive the wedge 512 when the end 51 of the body of the drive tool is inserted into the conduit 211.

Advantageously, the wedge 512 inserted into the notch 212 of the conduit 211 prohibits any movement of rotation of the ring 2 relative to the end 51 of the body of the drive tool 5. This advantageously avoids any risk of torsional deformation of the envelope 1, caused by accidental rotation of the ring 2, which could compromise the leaktightness of the envelope, said rotation being able to be induced by the friction of the body of the connector piece 3 against the fold 14 of the opening 12 of the envelope 1 when the connector piece 3 is driven in rotation by the coupling piece 52 of the drive tool 5.

The wedge 512 also allows a good positioning of the drive tool 5 into the envelope 1.

From a design point of view, the ring 2 is fixed on the inner wall of the bag 11 via its end flange 22, of which the distal face is fixed by welding or adhesive bonding on the inner wall of the bag 11.

As has been described above, the connector piece 3 has, as illustrated in FIGS. 7 to 9, a tubular distal portion 32 which is continued by a proximal portion 31.

The tubular distal portion 32 has a cylindrical body 321 of circular external cross section defining an internal cavity that forms a receiving zone 323 (cavity) intended to receive the end of the percutaneous surgical instrument to which the drive tool 5 is to be coupled.

According to the invention, the length of the distal portion 32 is mainly defined in such a way that, when the connector piece 3 is in place, the free end 325 of the portion 32 is situated outside the envelope 1.

The external diameter of the cylindrical body 321 is, for its part, defined so as to be slightly greater than the diameter of the opening 12 formed in the wall of the envelope 1, such that the insertion of the free end of the distal portion 32 of the connector piece 3 into the opening 12 causes an elastic deformation of the latter, forming a fold 14 around the outer wall of the cylindrical body 321, which fold is visible in FIG. 1. This fold contributes to ensuring the leaktightness of the envelope 1 in the area of the opening 12, by isolating the non-sterile zone delimited by the envelope 1 and the external space considered to be sterile.

In the embodiment taken as an example, the cavity 323 is a cavity of hexagonal cross section, on the walls of which are formed, in the area of the end 325, openings 324 permitting the engagement of fixing stubs which are placed at the end of the percutaneous surgical instrument. The endpiece of the percutaneous surgical instrument can then, for example, have the shape of a cylinder with a hexagonal base, intended to be received in a cylindrical cavity with hexagonal walls, which is formed in a given means of rotation.

The length of the endpiece of the instrument, the depth of the cavity and the general dimensions of the portions of the endpiece and of the cavity are principally defined in such a way that the biopsy instrument and the means of rotation are joined to each other without play, such that the use of said means, handle or tool with rotary connector piece, by the practitioner causes a rotation of the instrument about its axis of symmetry and causes the instrument to penetrate in a substantially rectilinear direction.

The proximal portion 31 is, for its part, configured and dimensioned to form the connection, with minimum play, between the connector piece 3 and the coupling piece 52 situated at the end of the body of the drive tool 5. The connection to the coupling piece 52 is provided by the outer wall of the proximal portion.

According to the invention, the proximal portion 31 moreover defines an internal cavity which continues the cavity 323 of the distal portion 32, as is illustrated in FIG. 1, such that the endpiece of the percutaneous surgical instrument is able to fit completely within the connector piece 3. This cavity is closed towards the end of the proximal portion that is intended to interface with the coupling piece 52 of the drive tool 5.

In the illustrative embodiment in question, the outer wall of the proximal portion 31 forms a male element of hexagonal cross section, dimensioned in such a way as to be inserted, with minimum play, into the hexagonal indentation 523 of the coupling piece 52 illustrated in FIGS. 2*a* and 3*a*.

Its outer wall also has a frustoconical zone 315 which is configured and arranged on the wall in such a way as to interact with the front end 522 of frustoconical shape of the coupling piece 52 of the drive tool 5, when the coupling piece is in place on the connector piece 3. The frustoconical zone 315 then engages in the front end 522 of the coupling piece 52 in such a way as to maintain, without play, the coaxiality of the two elements 3 and 52 during use.

In the illustrative embodiment described here, the body 311 of the proximal portion 31 also has, in the area of its end, a cylindrical end element 33 which is slit along its length and which is intended to be inserted in the blind cylindrical bore 526 forming the bottom of the coupling piece 52 of the drive tool 5.

Preferably, the diameter of the bore 526 is slightly greater than the diameter of the cross section of the end element 33.

However, the outer wall of the end element 33 moreover has bosses 332 forming overthicknesses, such that the diameter of the cross section of the end element is locally greater than the diameter of the bore 526. Nevertheless, the presence of the slit 331 allows the end element 33 to be made deformable such that, when the connector piece 3 is coupled to the coupling piece 52 of the drive tool 5, the bosses 332 rub against the wall of the bore 526, which advantageously avoids the possibility of the connector piece 3 moving freely in the coupling piece 52.

Furthermore, the body 311 of the proximal portion 31 has, on its outer wall, chamfered bosses 312 which are configured to be able to fit in the chamfered groove 524 formed in the inner wall of the cavity 521 in the area of the hexagonal rear zone 523 of the coupling piece 52 and to ensure that the body 311 of the proximal portion 31 of the connector piece 3 is blocked with a snap-fit action in the coupling piece 52.

According to the invention, the chamfered bosses 312 have chamfers 313 and 314, which may be identical or different.

The value of the angles of inclination of these chamfers makes it possible to regulate the force of insertion or extraction of the connector piece 3 in or out of the coupling piece 52. This force, of about 2 kg, is defined by the height of the chamfered bosses 312 in relation to the size of the hexagonal indentation 523 of the coupling piece 52.

These chamfered bosses 312 can be four in number, for example, distributed symmetrically about the wall of the body 311, and fit in the chamfered groove 524 of the coupling piece 52.

According to the invention, the connector piece 3 also has, as has been mentioned above, a blocking means configured to interact with the ring 2 in such a way as to limit the movement of translation of the connector piece 3 inside the ring 2.

In the present illustrative embodiment, the blocking means consists of an annular protuberance 34 arranged on the outer surface of the endpiece and placed in a plane perpendicular to the longitudinal axis of the connector piece 3, at the limit between the distal portion 32 and the proximal portion 31. This protuberance is dimensioned in such a way that, when the connector piece 3 shifts in the ring 2 from the inside to the outside of the bag 11, the endpiece will abut, at the end of its travel, against the wall of the flange 22 of the ring 2.

The annular protuberance 34 also makes it possible to ensure that particles do not propagate on the distal portion 32 of the connector piece 3 during its insertion into the coupling piece 52.

It additionally contributes to forming a system of baffles in the area of the opening 12 of the envelope 1, which reduces the risk of particles emerging from the envelope 1 when the device is assembled.

It also ensures that the ring 2 and the connector piece 3 are indeed placed coaxially, such that the deformation of the opening 12 of the envelope 11 is uniformly distributed about the cylindrical body 321 of the connector element 3.

In a particular embodiment, the device according to the invention can have an indicator ring 6, such as is illustrated in FIG. 10.

The indicator ring 6, of a colour different than the other elements of the device, snap-fits into a groove 322 located in the area of the cylindrical body 321 of the distal portion 32 of the connector piece 3.

The internal diameter 61 of the ring 6 is greater than or equal to the diameter of the groove 322, while being smaller than the external diameter of the cylindrical body 321. The external diameter 62, for its part, is greater than the external diameter of the cylindrical body 321, in such a way as to ensure retention of the bag 11 in the area of the opening 12.

The width of the indicator ring 6 is also smaller than the width of the groove 322.

The difference in colour allows the practitioner to confirm at a glance that the indicator ring 6 is visible and thereby to verify that the bag occupies a correct position in the zone of the first opening 12 of the envelope, said position guaranteeing good leaktightness of the device.

As the above description aims to show, the structure of the device according to the invention thus advantageously makes it possible, in particular in the preferred embodiment taken as an example, to guarantee leaktightness between the zone of the space limited by the envelope 1, and capable of enclosing a non-sterile material (the drive tool in particular), and the rest of the space in which the device is used, which space is in principle sterile.

In light of the technical features of the coupling device according to the invention, it is thus advantageously possible to easily couple a drive tool 5, a non-sterile tool, to a necessarily sterile biopsy instrument in a removable manner without risk of accidentally contaminating the sterile environment during the operation of coupling or the reverse operation of separation.

It should be noted here that, in light of the close relationship existing necessarily between the structures of the respective ends of the connector piece 3 of the device according to the invention and of the coupling piece 52 of the rotary drive tool 5, which are intended to interact to ensure the joining of these two elements, the invention relates not only to a coupling device having technical and morphological features rendering it capable of effecting removable coupling of a drive tool 5, a non-sterile tool, to a necessarily sterile biopsy instrument by guaranteeing the confinement of the drive tool, but also to an assembly making it possible to ensure, in an optimal manner, the rotation of the biopsy instrument by the drive tool. Here, an optimal manner means a manner by which it is possible in particular to limit the play that may exist at the different interfaces forming the mechanical chain connecting the drive tool and the biopsy instrument.

Thus, the invention of course also relates to a system for sterile coupling between a biopsy instrument and a rotary drive tool for said instrument, the system comprising the coupling device discussed above and also the coupling piece 52 for coupling the biopsy instrument to a rotary drive means 5, as described in the present invention, the coupling piece allowing different means to be mounted removably on the instrument such that the practitioner can set the instrument in rotation, and also the coupling piece for coupling the rotary drive tool to a biopsy instrument as also described in the present description.

Figure 11:
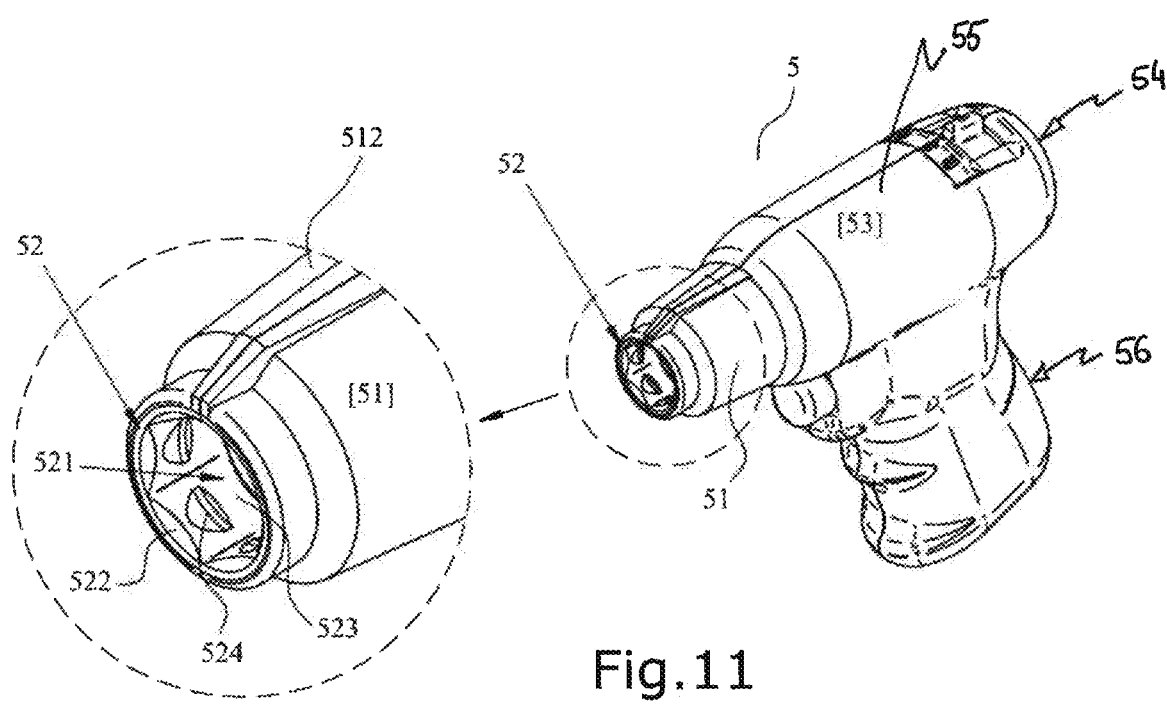
FIGS. 11 and 12 show schematic perspective views illustrating another example of the drive tool.
Figure 12:
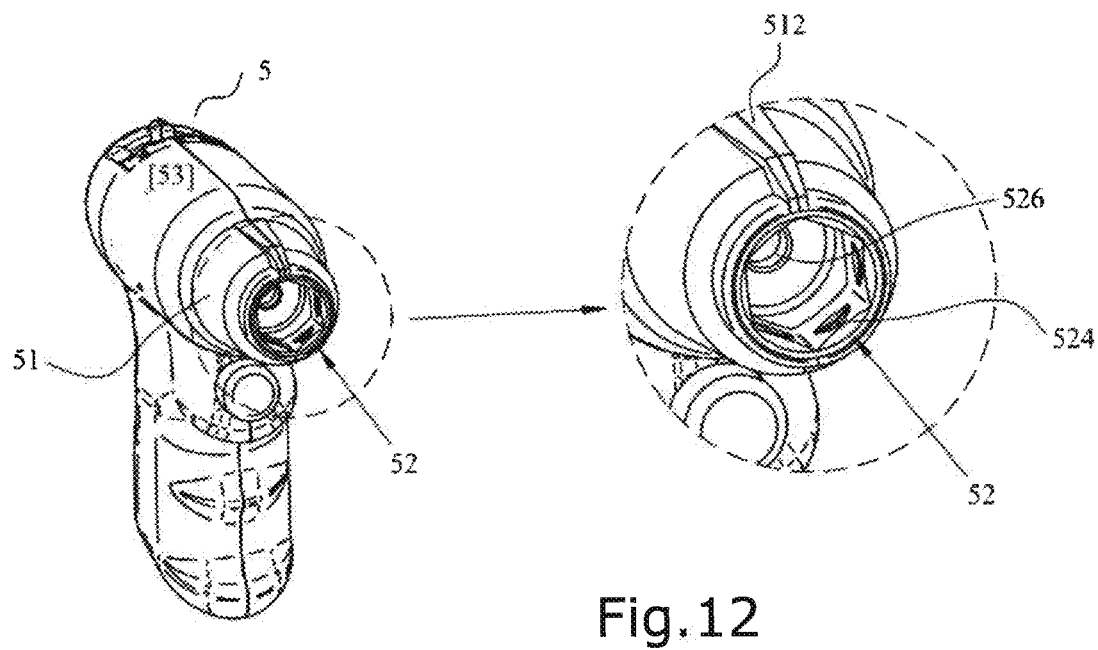
Figure 13:
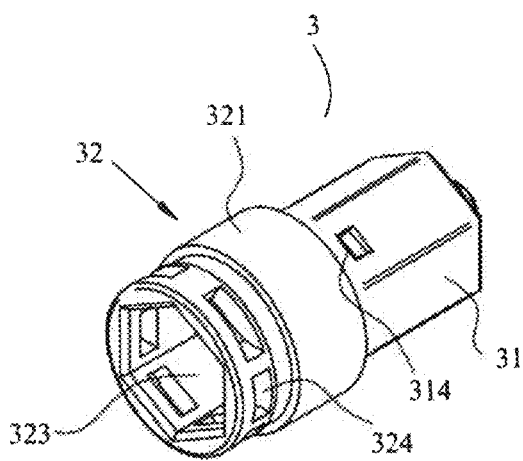
FIGS. 13 to 16 show schematic perspective views illustrating another example of connector piece.
Figure 14:
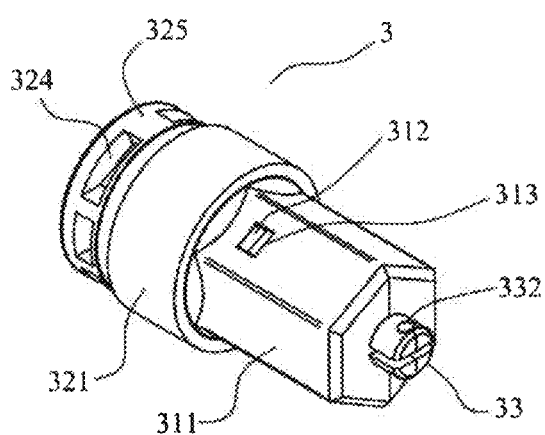
Figure 15:
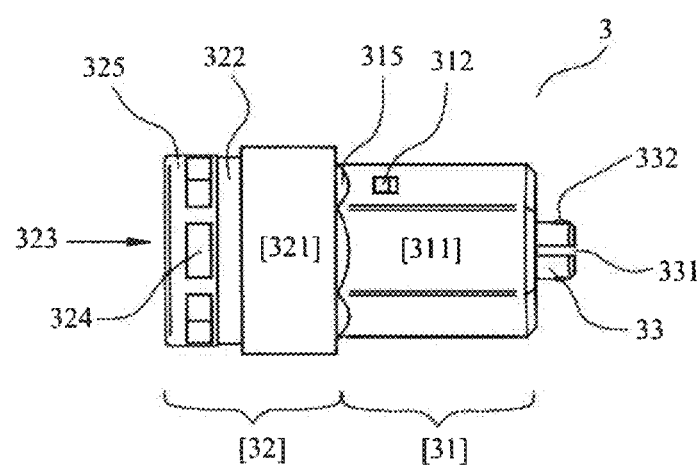
Figure 16:
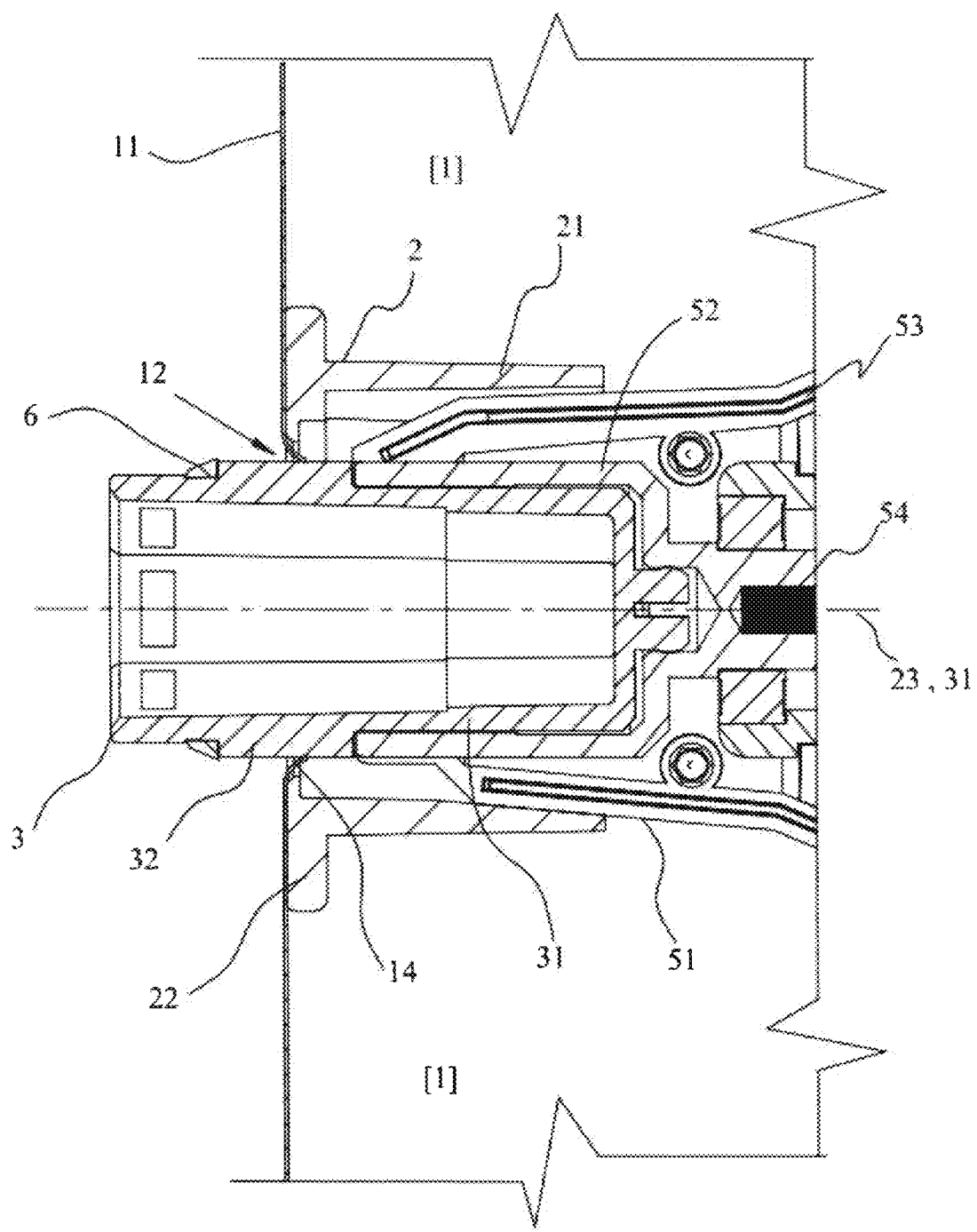

As illustrated on FIGS. 11 and 12, another embodiment of the rotary drive tool 5 is provided. The rotary drive tool 5 is presently described in a biopsy application but the rotary drive tool 5 can be broadly used in bone access applications. In this embodiment, the body 53 of the rotary drive tool 5 entirely covers the coupling piece 52 which therefore does not exit or extend from the end 51 of the body 53. In other words, the coupling piece 52 does not emerge from the body 53. Cleaning the rotary drive tool 5 is thus facilitated. Furthermore, this configuration wherein the coupling piece 52 does not exit from the body 53 prevents particles from being ejected from the rotary drive tool 5 into the envelope 1. Thus, it reduces the risk that a particle leaves the envelope 1 and contaminates the sterile percutaneous surgical instrument. The body 53 is preferably formed by two complementary-shaped shells forming two sides of the body 53 of the rotary drive tool 5.

The rotary drive tool 5 comprises a motor, preferably an electric motor, to drive in rotation the coupling piece 52, an accumulator to supply electricity to the motor, a reducer disposed between the motor and the coupling piece 52 to set the rotation speed and the torque transmitted to the coupling piece 52. The motor, the reducer and the accumulator are disposed within the body 53 of the rotary drive tool 5. Particularly, the motor and the reducer are disposed at an upper portion 54 of the body 53. The motor, the reducer and the coupling piece 52 are aligned with each other along a driving axis. The upper portion 54 is preferably cylindrical. Most preferably, the upper portion 54 comprises a central part 55 having a circular cross-section and enclosing the motor and the reducer. The diameter of the motor is preferably lower than the diameter of the reducer.

The rotary drive tool 5 further comprises a control circuit configured to control the motor, the reducer and the accumulator. The accumulator and the control circuit are preferably enclosed in a lower portion 56 of the rotary drive tool 5. This lower portion 56 forms a handle of the rotary drive tool 5.

The reducer is preferably configured to have a speed reducing ratio between 85:1 and 110:1, most preferably of 100:1. The motor and the reducer are preferably configured to make the coupling piece 52 to rotate at a rotation speed between 170 et 230 RPM, most preferably of 200 RPM. Furthermore, the motor and the reducer are preferably configured to transmit to the coupling piece 52 a torque between 3.5 and 7 Nm, most preferably of 4 Nm.

The embodiment of the rotary drive tool 5 of FIGS. 11 and 12 is the same as the embodiment of the rotary drive tool 5 of FIGS. 1 to 3a except the configuration of the body 53 as described above, particularly with the end 51 of the body 53 which fully covers the coupling piece 52.

From an operational point of view, the operation for the sterile coupling of a biopsy instrument and of a drive tool for said instrument by means of a coupling device according to the invention can be described by the following implementation steps:

A preliminary step in which the envelope 1 is turned back on itself, this step being carried out by pushing the ring 2 inside the envelope 1 until its free end 213 emerges from the envelope through the second opening 13 of the envelope 1;

a first step during which the assistant places the coupling piece 52 of the drive tool 5 on the proximal end 31 of the connector piece 3 until the two elements engage one inside the other, the sterile connector piece being disposed in such a way that the assistant does not have to come into contact with it;

a second step during which the practitioner, equipped with sterile gloves, takes hold of and presents the turned-back envelope 1 and during which the assistant, having introduced the distal end 51 of the drive tool 5, in which the end of the connector piece 3 is inserted, into the ring 2 of the envelope 1, lets go of the drive tool 5, the latter then being held by the practitioner via the turned-back envelope 1.

At this point, the end of the distal cylindrical portion 32 of the connector piece 3 passes through the cylindrical opening 12 of the envelope 1 causing its elastic deformation and ensuring the leaktightness of the envelope in the area of the opening 12.

At the same time, on account of the weight of the drive tool, the envelope 1 partially recovers its unfolded shape.

a third step during which the practitioner finishes reshaping the envelope 1 without touching the drive tool 5, such that the envelope 1 encloses the drive tool 5, then hermetically closes the second opening 13 of the envelope 1 with the aid of closure means arranged in the area of said opening;

a fourth step during which the practitioner fits the percutaneous surgical instrument in place by inserting the connector piece of said instrument in the end 323 of the distal portion 32 of the connector piece 3.

According to the invention, the preliminary step can either be carried out independently at the time or manufacture of the coupling device according to the invention, the device then being delivered to the practitioner in a sterile package with its envelope 1 already turned back, or it can be carried out by the practitioner just before its use, the device then being delivered in a sterile package with its envelope 1 not turned back on itself.

Considering in particular the coupling system presented by way of example in the above description, the first phase is in this case carried out by the assistant, who takes hold of the drive tool 5 and, after orienting it by means of the hexagonal visual indicator 525, slides it onto the end of the distal portion 31 of the connector piece 3, said connector piece then being held vertically, for example, in a medical packaging shell (i.e. blister pack) until the two elements click together.

The third step is carried out, for example, by the practitioner himself, who takes hold of one end of the envelope 1, then lifts it by causing the folded outer wall of the envelope 1 to slide in such a way as to enclose the drive tool 5, while taking care to ensure, however, that his fingers do not come into contact with the body 53 of the drive tool until the envelope 1 recovers its initial shape.

Thereafter, the practitioner closes the second opening 13 of the envelope 1, with the aid of the closure means arranged in the area of said opening, and checks that the indicator ring 6 is clearly visible, failing which the assembly that is formed would be considered to be defective.

Considering in particular the coupling system presented by way of example in the above description, the last phase of the coupling process involves the practitioner taking hold of the assembly formed by the drive tool 5 covered with the envelope 1, then inserting the hexagonal connector piece of the biopsy instrument into the hexagonal indentation 323 situated at the end of the distal portion 32 of the connector piece 3.

At the end of the last phase, the practitioner has available a sterile rotary tool which he can couple at will to a biopsy instrument, and he can then uncouple it from said instrument and replace it with a simple handle with which he can set the biopsy instrument in rotation without mechanical assistance.

As illustrated on FIGS. 13 to 16, a second embodiment of the connector piece 3 is provided. This second embodiment is the same as the embodiment of the connector piece 3 of FIGS. 7 to 9 except that the translation-blocking means or annular protuberance 34 is missing in the second embodiment. In this regard, the connector piece 3 can be inserted through the opening 12 of the envelope 1 without first being introduced within the envelope 1 by the second opening 13 of the envelope 1. In other words, the practitioner can insert the connector piece 3 through the opening 12 by the both sides of the opening 12. Hence, the practitioner can decide whether he wants to first connect the connector piece 3 to the rotary drive tool 5 or to first connect the rotary drive tool 5 to the ring 2 and then insert the connector piece 3 through the opening 12 to connect it to the rotary drive tool 5.

Inserting the connector piece 3 from the outside or from the side of the envelope on which the ring 2 is not attached to the inside of the envelope 1 allows to set the orientation of the fold 14 which constitutes a seal. If you insert the connector piece 3 from the inside to the outside of the envelope 1 as shown in the embodiment of FIG. 1, the fold 14 is oriented toward the outside of the envelope 1. To the contrary, if the connector piece 3 is inserted from the outside to the inside of the envelope 1 as allowed by the second embodiment of the connector piece 3, the fold 14 is oriented toward the inside of the envelope 1, as shown on FIG. 16. A fold 14 oriented toward the inside of the envelope 1 allows the fold 14 to withstand a better resistance to the pressure of the air trapped in the envelope 1. Thus, the fold 14 may provide a better sealing. On FIG. 16, the second embodiment of the connector piece 3 is coupled in the embodiment of the rotary drive tool as shown on FIGS. 11 and 12.

Figure 17:
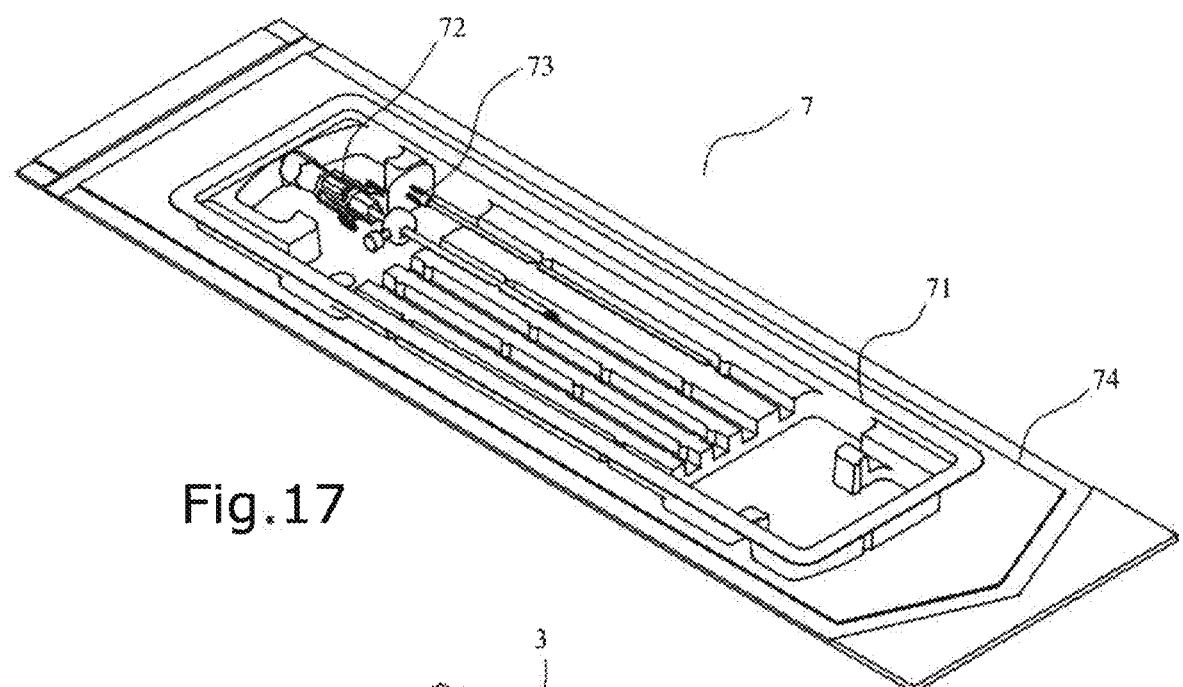
FIGS. 17 and 18 show schematic perspective views illustrating a kit comprising an instrument tray 7 and a connecting tray 8.
Figure 18:
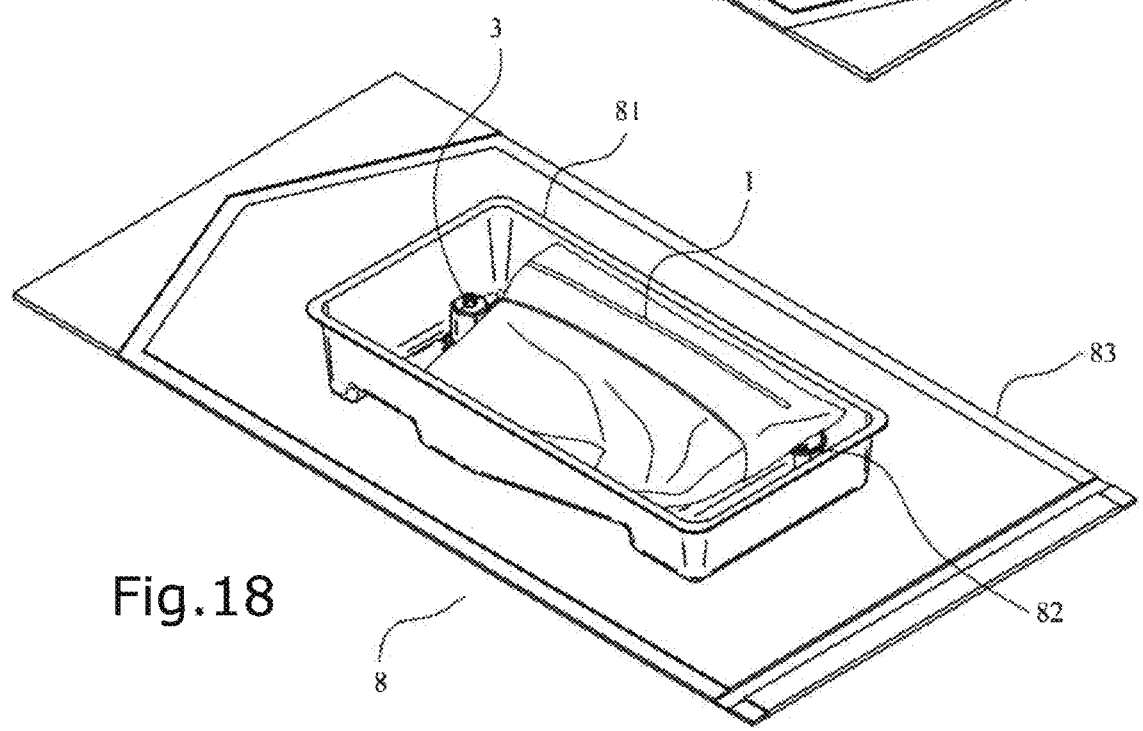

As shown on FIGS. 17 and 18, a kit comprising an instrument tray 7 and a connecting tray 8 is also provided.

The instrument tray 7 comprises at least one among a blister 71 intended to receive and hold surgical instruments, a trocar 72 enabling access through the bone and biopsy, an ejector 73 to eject a sample from a canula and a peelable pouch 74 to maintain the sterility of all the members that are inserted therein. The peelable pouch 74 is for example in polyethylene (as in "Tyvek"®) or paper.

According to a particular arrangement, the instrument tray 7 comprises instruments corresponding to the characteristics defined on a label disposed onto the instrument tray 7, for example a kit "11/10" has a trocar with an external diameter of 11 gauges and a maximum depth of use of 10 cm.

The connecting tray 8 comprises at least one among a blister 81 intended to receive and hold surgical components, a connector piece 3, a folded envelope 1, an ejector guide 82 to guide the ejector on one end of the canula, a peelable pouch 83 to maintain the sterility of all the members that are inserted therein. As the peelable pouch 74, the peelable pouch 83 s for example in polyethylene (as in "Tyvek"®) or paper.

In the connecting tray 8, the connector piece 3 is preferably not already inserted in the opening 12 of the envelope 1. This avoids any risk of permanent deformation of the opening 12 of the envelope 1 due to the effects of sterilization and the lifespan of the product. These deformations would render the sealing function of the envelope 1 by elastic deformation of the opening 12 around of the connector piece 3 ineffective.

The invention claimed is:

1. A rotary drive tool for coupling of a surgical instrument, the rotary drive tool being intended to be enclosed within an envelope in such a way that the rotary drive tool can be used in a sterile environment, the rotary drive tool comprising:
    a body comprising an end configured to removably engage the envelope intended to enclose the rotary drive tool,
    a coupling piece disposed within the body, the coupling piece being configured to engage and drive in rotation a surgical instrument,
    wherein the end of the body entirely covers the coupling piece such that the coupling piece does not extend from the end of the body.

2. The rotary drive tool according to claim 1, wherein the end of the body is configured to removably engage a ring fixed to a bag comprising an opening to receive the surgical instrument, the ring and the bag forming the envelope.

3. The rotary drive tool according to claim 2, wherein the end of the body is configured to prohibit any movement of rotation of the ring relative to the end of the body.

4. The rotary drive tool according to claim 3, wherein an outer surface of the end of the body comprises a longitudinal wedge configured to engage a longitudinal notch of the ring to prohibit any movement of rotation of the ring relative to the end of the body.

5. The rotary drive tool according to claim 1, wherein the end of the body has a conical shape.

6. The rotary drive tool according to claim 1, further comprising:
    a motor to drive in rotation the coupling piece,
    a reducer disposed between the motor and the coupling piece to set a rotation speed and a torque transmitted to the coupling piece by the motor.

7. The rotary drive tool according to claim 6, wherein the body comprises an upper portion having a central part enclosing the motor and the reducer, the central part having a circular cross-section.

8. The rotary drive tool according to claim 6, wherein the reducer has a speed reducing ratio between 85:1 and 110:1.

9. The rotary drive tool according to claim 8, wherein the reducer has a speed reducing ratio of 100:1.

10. The rotary drive tool according to claim 6, wherein the motor and the reducer are configured to make the coupling piece to rotate at a rotation speed between 170 and 230 RPM.

11. The rotary drive tool according to claim 10, wherein the motor and the reducer are configured to make the coupling piece to rotate at a rotation speed of 200 RPM.

12. The rotary drive tool according to claim 6, wherein the motor and the reducer are configured to transmit to the coupling piece a torque between 3.5 and 7 Nm.

13. The rotary drive tool according to claim 12, wherein the motor and the reducer are configured to transmit to the coupling piece a torque between is 4 Nm.

14. The rotary drive tool according to claim 1, further comprising:
    an accumulator to supply electricity to the motor,
    a control circuit configured to control the motor, the reducer and the accumulator.

15. The rotary drive tool according to claim 14, wherein the body comprises a lower portion forming a handle of the rotary drive tool and enclosing the accumulator and the control circuit.

* * * * *